United States Patent
Imai et al.

(10) Patent No.: US 6,451,492 B2
(45) Date of Patent: Sep. 17, 2002

(54) INSPECTION APPARATUS AND METHOD

(75) Inventors: Yutaka Imai; Ayumu Taguchi, both of Tokyo; Hitoshi Tamada; Hiroyuki Wada, both of Kanagawa, all of (JP)

(73) Assignee: Sony Corporation, Tokyo (JP)

(*) Notice: Subject to any disclaimer, the term of this patent is extended or adjusted under 35 U.S.C. 154(b) by 68 days.

(21) Appl. No.: 09/727,144

(22) Filed: Nov. 30, 2000

(30) Foreign Application Priority Data

Dec. 3, 1999 (JP) .......................... 11-345466

(51) Int. Cl.[7] .............................. G03F 9/00; G06K 9/00
(52) U.S. Cl. ...................... 430/30; 382/145; 382/149; 382/151
(58) Field of Search ............... 430/30; 382/145, 382/147, 148, 149, 151

(56) References Cited

U.S. PATENT DOCUMENTS 5,841,543 A  11/1998  Paradis, et al. ............. 356/394
5,864,394 A  1/1999   Jordan, III et al. ......... 356/237

FOREIGN PATENT DOCUMENTS

EP  0469765  2/1992
EP  0628806  12/1994
EP  0947881  10/1999

*Primary Examiner*—Christopher G. Young
(74) *Attorney, Agent, or Firm*—Sonnenschein, Nath & Rosenthal

(57) ABSTRACT

The imaging magnification of an imaging optical system 6 is set such that the image resolution of an ultraviolet CCD camera 5 is within a range from 10 nm to 30 nm, on a resist pattern 102 to be inspected. In addition, every time when the ultraviolet CCD camera 5 picks up an image, the resist pattern 102 to be inspected is irradiated at an irradiation light amount within a range from 0.5 mJ/cm$^2$ to an irradiation threshold value at which the resist pattern 102 is not caused to contract or an irradiation threshold value at which an absorption rate of an anti-reflection film provided near the resist pattern is not caused to change.

13 Claims, 5 Drawing Sheets

INSPECTION APPARATUS AND METHOD

RELATED APPLICATION DATA

The present application claims priority to Japanese Application No. P11-345466 filed Dec. 3, 1999, which application is incorporated herein by reference to the extent permitted by law.

BACKGROUND OF THE INVENTION

The present invention relates to an inspection apparatus and an inspection method suitable for inspecting the state of a resist pattern formed on a semiconductor wafer in a lithography step in semiconductor process.

In recent years, the integration rate of semiconductor integrated circuit has been improved as digitalization has been developed in the electric industrial field. How this highly integrated semiconductor circuit can be efficiently supplied at low costs is a significant problem that will decide future progress in the digital electronic industrial field.

To produce efficiently semiconductor integrated circuits at low costs, it is important to detect rapidly and correctly problems which occur during the manufacturing process. Therefore, there is a greater demand for an inspection apparatus capable of inspecting a micro pattern.

Known as inspection apparatuses having a high resolution are those using a scanning electron microscope (SEM), an atomic force microscope (AFM), and the like. However, these scanning electron microscopes and atomic force microscopes require vacuum in inspection, and are therefore inconvenient for handling. In addition, it takes much time to inspection entirely a semiconductor device.

In contrast, an inspection apparatus using an optical microscope is advantageous in that inspection can be carried out undestructively without necessitating vacuum or contact. In recent years, developments have been made in a ultraviolet solid laser apparatus which performs waveconversion on a YAG laser or the like with use of non-linear optical crystal thereby to emit laser light having a wavelength of a ultraviolet range. If this ultraviolet solid laser apparatus is used as an illumination light source and if an optical system is constructed by using an objective lens having a high NA, even an optical microscope can attain a resolution close to that of a scanning electronic microscope. Hence, expectation is much devoted to the optical microscope.

Meanwhile, it is desired that inspection of a pattern of a semiconductor integrated circuit should be carried out with a resist pattern formed on a semiconductor wafer. This resist pattern is formed in a manner that resist material coated on a semiconductor wafer is exposed by an exposure apparatus and developed, in accordance with a pattern to be formed.

Suppose a case that a resist pattern as described above is inspected by an inspection apparatus which inspects an inspection target by picking up an image of the inspection target by an image pickup element such as a CCD (charge-coupled device) camera or the like, with an ultraviolet solid laser apparatus used as an illumination light source. In this case, the wavelength of illumination light is close to the wavelength of a light source of an exposure apparatus. Therefore, the resist pattern to be detected may contract in response to the illumination light if the irradiation light amount of the illumination light is large. Although an anti-reflection film is normally provided in the vicinity of the resist pattern in order to prevent abnormal exposure due to reflection during exposure, the absorption rate of this anti-reflection film changes thereby influencing harmfully the inspection of the resist pattern, if the irradiation light amount of the illumination light is large.

On the other side, if the irradiation light amount of the illumination light is too small when a resist pattern is inspected by the above-described inspection apparatus, the noise component of the image pickup element is large relatively to the obtained signal component, so that the resist pattern cannot be inspected with good accuracy in some cases.

Consequently, it is important to control the irradiation light amount of the illumination light to a proper value, in order to inspect the resist pattern by the above-described inspection apparatus.

BRIEF SUMMARY OF THE INVENTION

The present invention has been proposed in view of the situation described above and has an object of providing an inspection apparatus and an inspection method capable of inspect a resist pattern accurately and properly by irradiating illumination light at a proper irradiation light amount on a resist pattern to be inspected.

An inspection apparatus according to the present invention comprises: illumination means for irradiating a resist pattern as an inspection target with illumination light having a wavelength of 355 nm or less within an ultraviolet range; image pickup means for picking up an image of the resist pattern illuminated by the illumination means; an imaging optical system for forming an image of the resist pattern illuminated by the illumination means; and image processing means for processing the image of the resist pattern picked up by the image pickup means.

In this inspection apparatus, the imaging magnification of the imaging optical system is set such that the image resolution of the image pickup means falls in a range from 10 nm to 30 nm on the resist pattern. The "image resolution" means a value expressing how large area on the resist pattern as an inspection target one minimum image pickup unit (one pixel) of the image pickup means corresponds to. In this inspection apparatus, the imaging magnification is set such that the image resolution of the image pickup means falls in a range from 10 nm to 30 nm.

Also, in this inspection apparatus, the illumination means irradiates the resist pattern with the illumination light at an irradiation light amount within a range from 0.5 mJ/cm$^2$ to an irradiation threshold value at which the resist pattern is not caused to contract or an irradiation threshold value at which an absorption rate of an anti-reflection film provided near the resist pattern is not caused to change, every time when the image pickup means picks up an image.

According to this inspection apparatus, a resist pattern as an inspection target is illuminated with illumination light having a wavelength of 355 nm within an ultraviolet range. Further, an image of the resist pattern illuminated with the illumination light having a wavelength within the ultraviolet range is guided to and formed by the image pickup means. At this time, the image resolution of the image pickup means corresponds to an area ranging from 10 nm to 30 nm.

The image of the resist pattern picked up by the image pickup means is taken in and processed by the image processing means. The image of the resist pattern thus processed by the image processing means is an image of the resist pattern illuminated with the illumination light having a wavelength within an ultraviolet range, which is light having a very short wavelength. Therefore, the state of the resist pattern can be inspected very accurately by analyzing the image of the resist pattern processed by the image processing means.

Also, in the inspection apparatus according to the present invention, the illumination means irradiates illumination light on the resist pattern at an irradiation light amount within the range described above, every time when the image pickup means picks up one image. Therefore, the noise component of the image pickup element can be reduced relatively to the signal component, so that the inspection accuracy can be improved. In addition, contraction of the resist pattern and change of characteristics of the anti-reflection film can be prevented effectively so that inspection of the resist pattern can be carried out properly.

That is, if the resist pattern is not irradiated with an irradiation light amount equal to or higher than 0.5 mJ/cm$^2$ every time when the image pickup means picks up an image, the ratio of the noise component to the signal component becomes too high to inspect accurately the resist pattern, in an inspection apparatus in which the image resolution of the image pickup means on the resist pattern is set within a range from 10 nm to 30 nm.

If the irradiation light at which the resist pattern is irradiated with illumination light every time when the image pickup means picks up an image exceeds an irradiation threshold value at which the resist pattern is not caused to contract, the resist pattern causes contraction. If it exceeds an irradiation threshold value at which the absorption rate of the resist pattern is not caused to change, the absorption rate of the resist pattern changes. In any cases, proper inspection is hindered.

In the inspection apparatus according to the present invention, the illumination means irradiates the resist pattern with the illumination light at the irradiation light amount within the range from 0.5 mJ/cm$^2$ to the irradiation threshold value at which the resist pattern is not caused to contract or the irradiation threshold value at which the absorption rate of the anti-reflection film provided near the resist pattern is not caused to change, every time when the image pickup means picks up an image. Therefore, the resist pattern can be inspected accurately and properly.

In an inspection method according to the present invention, illumination light is irradiated on a resist pattern as an inspection target with illumination light, an image of the resist pattern thus illuminated is picked up by image pickup means, and the image of the resist pattern picked up by the image pickup means is processed and analyzed, thereby to inspect a state of the resist pattern.

Further, in this inspection method, the resist pattern is irradiated with illumination light having a wavelength of 355 nm or less within an ultraviolet range at an irradiation light amount within a range from 0.5 mJ/cm$^2$ to an irradiation threshold value at which the resist pattern is not caused to contract or an irradiation threshold value at which an absorption rate of an anti-reflection film provided near the resist pattern is not caused to change, every time when the image pickup means picks up an image, and the image of the resist pattern illuminated with the illumination light is formed on the image pickup means with use of an image optical system in which an imaging magnification is set such that an image resolution of the image pickup means falls within a range from 10 nm to 30 nm.

According to this inspection method, the image of the resist pattern illuminated with the illumination light having a wavelength within an ultraviolet range, which is light having a very short wavelength, is processed and analyzed thereby to inspect the state of the resist pattern. Therefore, the state of the resist pattern can be inspected very accurately.

Also, according to this inspection method, every time when the image pickup means picks up an image, the illumination means irradiates the resist pattern with the illumination light at the irradiation light amount within the range from 0.5 mJ/cm$^2$ to the irradiation threshold value at which the resist pattern is not caused to contract or the irradiation threshold value at which the absorption rate of the anti-reflection film provided near the resist pattern is not caused to change. Therefore, while maintaining a sufficient signal component in relation to the noise component of the image pickup element, contraction of the resist pattern and change of characteristics of the anti-reflection film can be restricted effectively so that the resist pattern can be inspected properly.

As has been explained above, according to the present invention, light having a short wavelength within an ultraviolet range is used as illumination light, to control the irradiation light amount to a proper value. Therefore, a resist pattern having a micro structure can be inspected properly and accurately, without causing contraction of the resist pattern or change of characteristics of an anti-reflection film provided near the resist pattern.

DETAILED DESCRIPTION OF THE INVENTION

In the following, embodiments of the present invention will be explained with reference to the drawings.

According to the present invention, a resist pattern formed on the semiconductor wafer or the like is illuminated with illumination light having a wavelength within an ultraviolet range, to pick up an image. The image thus picked up is subjected to processing and analysis, to detect edge positions of a resist pattern, so that the line width is managed or so.

The resist pattern formed on the semiconductor wafer has become more micro as the integration of the semiconductor integrated circuit or the like has been improved. To inspect optically this micro resist pattern with high accuracy, it is effective to use light having a short wavelength as illumination light. Hence, the present invention uses light having a short wavelength of 355 nm or less within an ultraviolet range as illumination light.

Thus, in case where a resist pattern is illuminated with light having a wavelength within an ultraviolet range, there is a problem that the resist pattern reacts with the illumination light and contracts if the irradiation light amount is large. Contraction of the resist pattern is caused suddenly when the irradiation light amount of the illumination light exceeds an irradiation threshold value. Therefore, even in case of using light having a wavelength within an ultraviolet range, inspection can be carried out properly without causing contraction of the resist pattern if the irradiation light amount of the illumination light when picking up an image is set to be equal to or lower than an irradiation threshold value at which the resist pattern does not cause contraction. At this time, the irradiation threshold value at which the resist pattern is not caused to contract varies depending on the kind of resist material being used.

Figure 1:
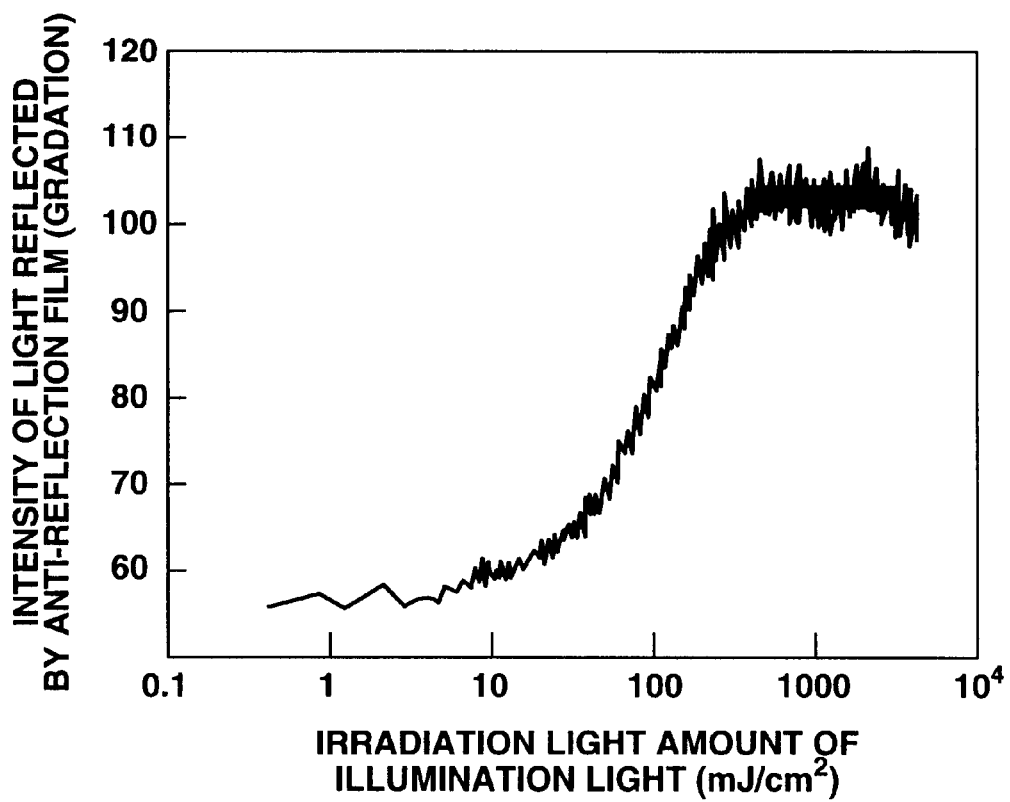
FIG. 1 is a graph showing a relationship between the irradiation light amount of illumination light and the intensity of light reflected by an anti-reflection film.

Normally, an anti-reflection film, by which reflection during exposure and formation of a resist pattern is prevented to form the resist pattern into an appropriate shape, is provided as an upper or lower layer of the resist pattern. In case where light having a wavelength within an ultraviolet range is irradiated as illumination light on a resist pattern, the absorption rate of the anti-reflection film is changed if the irradiation light amount is so large so as to exceed a predetermined value. As a result, the intensity of light reflected by the anti-reflection film is suddenly increased as shown in FIG. 1. If the intensity of the light reflected by the anti-reflection film is thus increased suddenly, the picked-up image of the resist pattern changes in accordance with the condition of the anti-reflection film, so that harmful influences can be made on the inspection accuracy. Therefore, in case of using light having a wavelength within an ultraviolet range as illumination light, it is important to illuminate the resist pattern at an irradiation light amount which does not cause the anti-reflection film to change its absorption rate.

From the above, it is required that the irradiation light amount of the illumination light for picking up an image must be set to be equal to or less than an irradiation threshold value at which a resist pattern is not caused to contract or an irradiation threshold value at which an anti-reflection film is not caused to change its absorption rate, in order to inspect a resist pattern, using light having a wavelength of 355 nm or less within an ultraviolet range as illumination light.

For example, in case of inspecting a resist pattern having a line width of about 150 nm in the step of forming a gate wiring of a semiconductor integrated circuit with use of a deep ultraviolet laser beam having a wavelength of about 266 nm as illumination light, the irradiation light amount of the illumination light for picking up an image should be set preferably to 20 to 30 mJ/cm$^2$ or less or more preferably to about 1 mJ/cm$^2$.

Meanwhile, if a resist pattern is inspected with weak light by reducing the irradiation light amount of the illumination light for picking up an image (herein after called weak light inspection), a problem lies in noise of the image pickup element such as a CCD camera or the like which picks up an image. That is, in the weak light inspection, the light amount which enters into the CCD camera is small, so that the ratio of the noise component increases relatively to the signal component. This noise component becomes a factor which deteriorates the inspection accuracy.

The noise of the CCD camera includes shot noise electronically generated when photoelectrically converting light which has entered into the CCD camera, read noise generated when transferring image data picked up by the CCD camera to an image processing means of an image processing computer, heat noise, and the like. The read noise and heat noise of the CCD camera can be effectively restricted by cooling the chip of the CCD camera. For example, read noise and heat noise of the CCD camera can be greatly reduced by the chip of the CCD camera to 5° C. or less by use of a Peltier element, compared with the case of using it at an ordinary temperature.

On the other side, a countermeasure must be taken by improving the quantum efficiency with respect to the shot noise which is generated when light entering into the CCD camera is photoelectrically converted. For example, the CCD camera is constructed with use of a CCD chip which shows high quantum efficiency within an ultraviolet range, and this CCD camera is used as an image pickup element. In this manner, it is possible to reduce the shot noise ratio with respect to the amount of the light received by the image pickup element. The quantum efficiency of a CCD camera means the ratio of the number of generated electrons to the number of incident photons, including the surface transmittance, internal absorption, and photoelectric conversion rate, and the like.

However, there is a limitation to the level of shot noise that can be reduced by improving the quantum efficiency of the CCD camera. It is difficult to reduce the noise to be lower than the limitation. Therefore, in case where a resist pattern is illuminated with illumination light having a wavelength within an ultraviolet range and an image of the resist pattern is picked up by a CCD camera to inspect the resist pattern, the ratio of the shot noise to the signal component, which cannot be reduced due to improvements of the quantum efficiency of the CCD camera, is enlarged if the amount of the illumination light irradiated on the resist pattern is too small. As a result, the inspection accuracy is deteriorated.

Hence, in case where a resist pattern is illuminated with illumination light having a wavelength within an ultraviolet range and an image of the resist pattern is picked up by a CCD camera to inspect the resist pattern, the shot noise ratio must be lowered to a constant level or less by illuminating the resist pattern with a constant irradiation light amount or more so that an amount of light enough to maintain the inspection accuracy enters into the CCD camera.

Meanwhile, the number of photons that enter into one minimum image pickup unit (1 pixel) of a CCD camera is not determined uniformly by the irradiation light amount of the illumination light but also depends on the imaging magnification of an imaging optical system for forming an image of a resist pattern illuminated with illumination light on the CCD camera. That is, if the irradiation light amount of the illumination light is constant, the number of photons that enter into one pixel of the CCD camera increases and the ratio of the signal component to the shot noise also increases as the imaging magnification of the imaging optical system is lower.

However, the imaging magnification of the imaging optical system is a parameter which determines the image resolution. If the imaging magnification of the imaging optical system is too low, an area on the resist pattern, which corresponds to one example, becomes so large that it is difficult to inspect accurately a micro structure.

For example, in order to inspect accurately a resist pattern having a line width of about 150 nm in a step of forming a gate wire of a semiconductor integrated circuit with use of deep ultraviolet laser beam having a wavelength of about 266 nm as illumination light, the imaging magnification should preferably be set such that the image resolution of the CCD camera is within a range from 10 nm to 30 nm or is more preferably about 24 nm.

Figure 2:
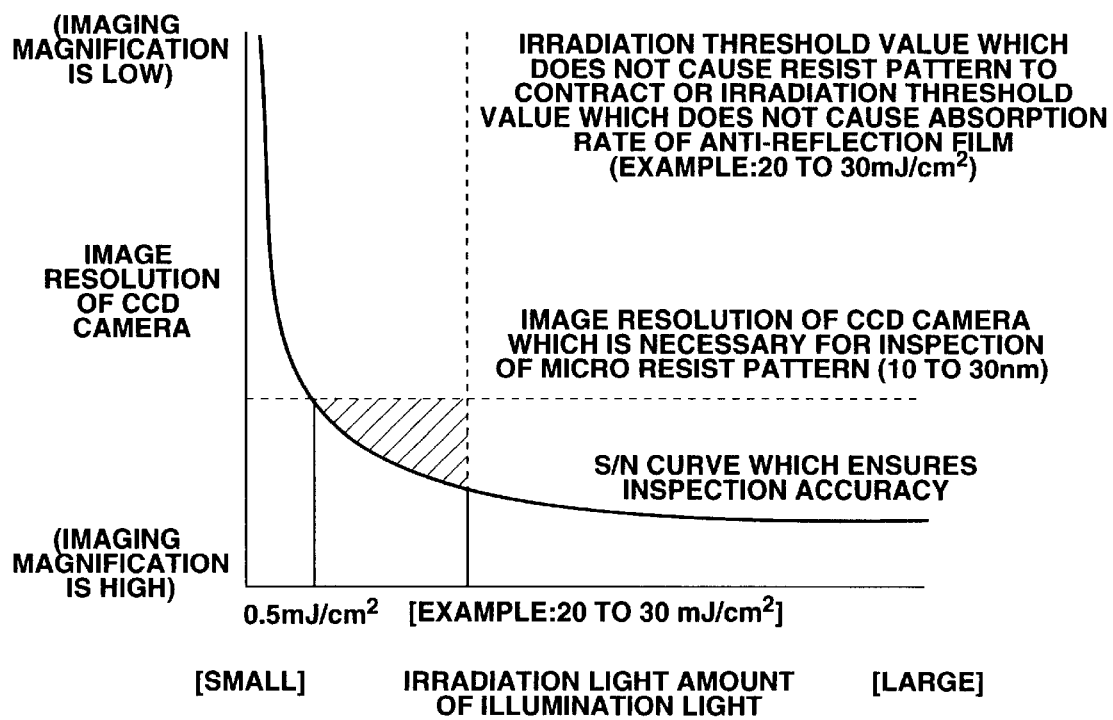
FIG. 2 is a graph which explains an optimal range of the irradiation light amount of the illumination light.

If the imaging magnification of the imaging optical system is set such that the image resolution of the CCD camera falls in the range as described above, the resist pattern must be illuminated at an irradiation light amount of about 0.5 mJ/cm$^2$ or more, as shown in FIG. 2, in order to maintain an inspection accuracy by increasing the ratio of the signal component to the shot noise.

In view of various situations described above, the present invention is arranged as follows. That is, the imaging magnification is set such that the image resolution of the CCD camera is within a range from 10 nm to 30 nm on the resist pattern, and the irradiation light amount of the illumination light irradiated on the resist pattern is set within a range from 0.5 mJ/cm$^2$ to an irradiation threshold value at which the resist pattern is not caused to contract or an irradiation threshold value at which an anti-reflection film provided near the resist pattern is not caused to change (the area indicated by hatching in FIG. 2). In this manner, a micro resist pattern can be inspected properly and accurately.

An inspection apparatus to which the present invention is applied will now be explained specifically.

Figure 3:
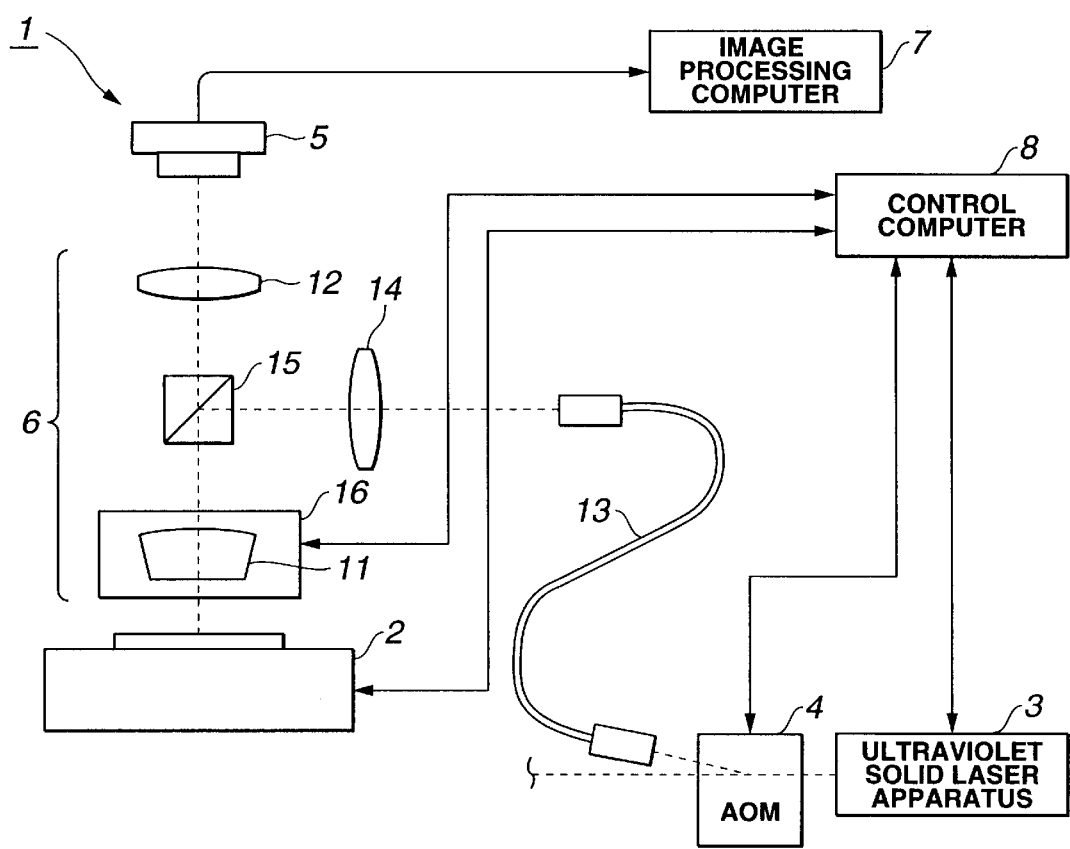
FIG. 3 is a structural view showing an example of an inspection apparatus to which the present invention is applied.

FIG. 3 shows a structural example of an inspection apparatus to which the present invention is applied. The inspection apparatus 1 shown in FIG. 3 serves to inspect the state of a resist pattern formed on a semiconductor wafer with an anti-reflection film inserted therebetween. The inspection apparatus comprises a movable stage 2 which supports a semiconductor wafer 100 where a resist pattern is formed, an ultraviolet solid laser device 3 which emits illumination light having a wavelength within an ultraviolet range, an acoustic optics modulator (AOM) 4 which acoustically modulates the illumination light emitted from the ultraviolet solid laser device 3, an ultraviolet CCD camera 5 which picks up an image of the resist pattern illuminated with the illumination light, an imaging optical system 6 which forms an image of the resist pattern illuminated with the illumination light, on the CCD camera 5, an image processing computer 7 which processes the image of the resist pattern picked up by the CCD camera 5, and a control computer 8 which controls operation of the entire inspection apparatus 1.

The movable stage 2 comprises, for example, X- and Y-stages for moving the semiconductor wafer 100 set on the movable stage 2 in the horizontal direction, a Z-stage for moving the semiconductor wafer 100 in the vertical direction, a è-stage for rotating the semiconductor wafer 100, and a suction plate for suctioning the semiconductor wafer 100 to fix it to the movable stage 2. Further, the movable stage 2 operates the other stages described above under control from the control computer 8, thereby to move the portion to be inspected of the semiconductor wafer 100 to a predetermined inspection position.

The ultraviolet solid laser device 3 performs wavelength-conversion on a solid laser such as a YAG laser or the like with use of a non-linear optical crystal, thereby to emit a deep ultraviolet (DUV) laser beam having a wavelength of about 266 nm, for example.

The inspection ability of the inspection apparatus depends on the wavelength of the illumination light to be irradiated on an inspection target. Illumination light with a shorter wavelength of the illumination light enables inspection of a more micro pattern. The inspection apparatus 1 uses an ultraviolet solid laser apparatus 3 as a light source of the illumination light, so that the semiconductor wafer 100 can be illuminated with a deep ultraviolet laser beam having a short wavelength. It is therefore possible to inspect a micro pattern. In addition, the ultraviolet solid laser device 3 itself has a small size and requires no water-cooling. Thus, the device 3 provides easy handling, and is suitable for a light source of illumination light. Note that a deep ultraviolet laser beam having a wavelength of 266 nm can be obtained as a quadruple wave of a YAG laser beam.

The acoustic optical modulator 4 is an optical modulator using an acoustic optical effect. In this acoustic optical modulator 4, the intensity of primary diffraction light in Bragg diffraction or Debye sheath effect is substantially proportional to the ultrasonic power. Therefore, the intensity of the primary diffraction light can be electrically adjusted by controlling an RF signal inputted to the acoustic optical modulator 4 to modulate the ultrasonic power. In the inspection apparatus 1, illumination light emitted from the ultraviolet solid laser device 3 is let enter into the acoustic optical modulator 4, and the primary diffraction light diffracted by this acoustic optical modulator 4 is irradiated as illumination light on a resist pattern as an inspection target. Further, in this inspection apparatus 1, the RF signal inputted to the acoustic optical modulator 4 is controlled by a control computer 8 thereby to adjust the irradiation light amount of the illumination light to be irradiated on the resist pattern.

The ultraviolet CCD camera 5 is, for example, a CCD camera constructed such that a high sensitivity can be attained with respect to ultraviolet light. For example, a quantum efficiency of about 30% or more is obtained with respect to a deep ultraviolet laser beam having a wavelength of about 266 nm. Also, the ultraviolet CCD camera 5 is structured such that the CCD chip is cooled to about 5° C. by a Peltier element. Thus, it is possible to reduce greatly read noise and heat noise which are caused when image data picked up by the ultraviolet CCD camera 5 is transferred to the image processing computer 7.

The imaging optical system 6 comprises an ultraviolet objective lens 11 and an imaging lens 12 and serves to form an image of a resist pattern, which is illuminated with illumination light, at a predetermined imaging magnification on the ultraviolet CCD camera 5. In the inspection apparatus 1 to which the present invention is applied, the imaging magnification of the imaging optical system 6 is set such that the image resolution of the ultraviolet CCD camera 5 is within a range from 10 nm to 30 nm on the resist pattern being inspected, i.e., an area of 10 to 30 nm on the resist pattern corresponds to one pixel of the ultraviolet CCD camera 5.

With use of the inspection apparatus 1 shown in FIG. 3, explanation will now be made of a method for inspecting a line width of a resist pattern formed on the semiconductor wafer 100 with an anti-reflection film inserted therebetween.

Figure 4:
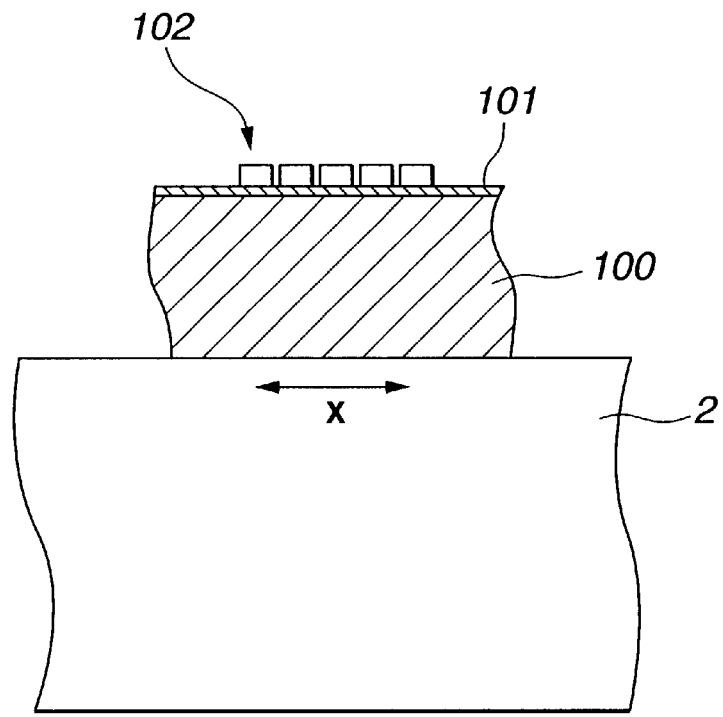
FIG. 4 is a schematic view showing a state where a resist pattern as an inspection target is set on a movable table of the inspection apparatus.

At first, as shown in FIG. 4, the semiconductor wafer 100 on which a resist pattern 102 is formed with an anti-reflection film 101 inserted therebetween is set on the movable table 2. Further, the movable table 2 is driven under control of the control computer 7, and motion of the semiconductor wafer 100 is controlled, so that the portion to be inspected of the resist pattern 102 is positioned at a predetermined inspection position.

Next, the ultraviolet solid laser device 3 is driven under control from the control computer 7, so as to emit a deep ultraviolet laser beam having a wavelength of about 266 nm from the laser device 3, for example. The ultraviolet laser beam emitted from the ultraviolet solid laser device 3 is incident to the acoustic optical modulator 4.

The acoustic optical modulator 4 modulates incident light under control from the control computer 8. Specifically, an RF signal inputted to the acoustic optical modulator 4 from the control computer 8 is controlled thereby to adjust the intensity of primary diffraction light of the deep ultraviolet laser beam which is transmitted through the acoustic optical modulator 4. In the inspection apparatus 1 to which the present invention is applied, the primary diffraction light is irradiated as illumination light onto the resist pattern 102 as an inspection target. By controlling the RF signal inputted to the acoustic optical modulator 4, illumination light is irradiated on the resist pattern 102 as an inspection target at an irradiation light amount within a range from 0.5 mJ/cm$^2$ to an irradiation threshold value at which the resist pattern 102 is not caused to contract or an irradiation threshold value at which the anti-reflection film 101 is not caused to change its absorption rate, every time when the ultraviolet CCD camera 5 picks up an image.

In this inspection apparatus 1, the irradiation light amount of the illumination light to be irradiated on the resist pattern 102 as an inspection target is controlled electrically with use of the acoustic optical modulator 4 controlled by the control computer 8. Therefore, the irradiation light amount of the illumination light can be controlled properly, simply, and easily. Also, in this inspection apparatus 1, illumination light can be irradiated on the resist pattern 102 as an inspection target, for example, in synchronization with the shutter of the ultraviolet CCD camera 5. Irradiation of illumination light can be performed efficiently.

The primary diffraction light (illumination light) which has been transmitted through the acoustic optical modulator 4 is introduced to the part of the optical system by an ultraviolet optical fiber 13. Further this illumination light is transmitted through a lens 14 and enters into a beam splitter 15. The illumination light reflected by the beam splitter 15 is irradiated on the resist pattern 102 of the semiconductor wafer 100 set on the movable table 2. In this manner, the resist pattern 102 as an inspection target is illuminated with the illumination light which is a deep ultraviolet laser beam whose light amount is controlled.

Figure 5:
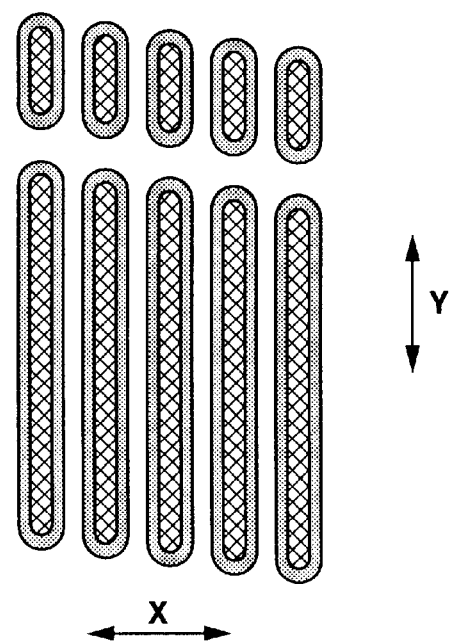
FIG. 5 is a view showing an image of a resist pattern picked up by an ultraviolet CCD camera of the inspection apparatus.

The reflection light from the resist pattern 102 illuminated by the illumination light is transmitted through the ultraviolet objective lens 11 and enters into the beam splitter 15. Further, the reflection light from the resist pattern 102, which has been transmitted through the beam splitter, enters into the ultraviolet CCD camera 5 through an imaging lens 12. In this manner, an image of the resist pattern, which is enlarged by the ultraviolet objective lens 11 as shown in FIG. 5, is picked up by the ultraviolet CCD camera 5.

For example, a lens having a high numerical aperture NA of about 0.9 is used as the ultraviolet objective lens 11. In this inspection apparatus 1, a deep ultraviolet laser beam having a short wavelength is used as the illumination light, and a lens having a high numerical aperture is used as the ultraviolet objective lens 11, thus enabling inspection of a more micro pattern. In addition, a countermeasure capable of reducing the aberration with respect to an ultraviolet light having a wavelength of about 266 nm is adopted in the ultraviolet objective lens 11.

The ultraviolet objective lens 11 is movable in the direction in which the lens comes closer to the resist pattern 102 as an inspection target, by a focus adjust mechanism 16 driven under control from the control computer 8. Therefore, the lens is arranged such that focus adjustment can be achieved by the control from the control computer 8.

The image of the resist pattern 102 picked up by the ultraviolet CCD camera 5 is taken in by the image processing computer 7. Further, the image processing computer 7 processes the image of the take-in resist pattern 102 thereby to prepare an intensity profile of light, as shown in FIG. 6.

Figure 6:
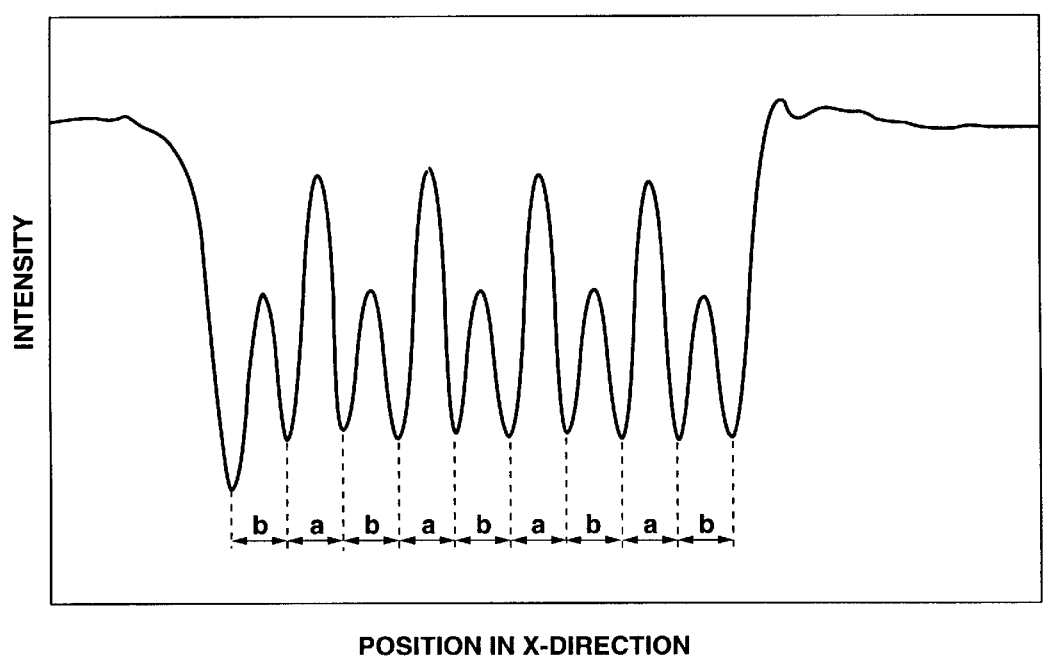
FIG. 6 is a graph showing an intensity profile prepared by an image processing computer, based on an image of a resist pattern picked up by the ultraviolet CCD camera.

The intensity profile shown in FIG. 6 is obtained when illumination light diffracted by the resist pattern 102 constructed by concaves and convexes causes interference near gaps therebetween. This profile corresponds to the concaves and convexes of the resist pattern 102. That is, the large crests appearing on the intensity profile (e.g., the portions indicated at the reference a in FIG. 6) correspond to concave portions of the resist pattern 102, and portions each appearing between two large crests (e.g., the portions indicated at the reference b in FIG. 6) on the intensity profile correspond to convex portions of the resist pattern 102. Also on the intensity profile, a small crest appears between every two large crests, and a peak as a trough appears between every adjacent small and large crests. The peaks as troughs correspond to boundary portions between concave and convex portions (hereinafter called pattern edges).

In the inspection apparatus 1 to which the present invention is applied, it is thus possible to obtain an intensity profile on which peaks as troughs appear in correspondence with pattern edges of the resist pattern 102. It is therefore possible to measure the width (line width) of each convex portion of the resist pattern 102 from the intensity profile. That is, on the intensity profile obtained by the inspection apparatus 1, the portion sandwiched between two peaks as troughs corresponds to the width of a convex portion. Accordingly, a line width of the resist pattern 102 can be measured by obtaining the distance between two peaks as troughs.

Explained now will be a method of measuring a line width of the resist pattern 102 from an intensity profile prepared by the image processing computer 7.

To measure a line width of the resist pattern 102 from an intensity profile prepared by the image processing computer 7, at first, the part of a trough of the intensity profile is fitted to a quadric function. Further, an extreme of the quadric function is detected as a peak of a trough portion. In this manner, it is possible to obtain the positions of peaks of trough portions, which correspond to pattern edges of the resist pattern 102, with a high accuracy equivalent to the pixel size of the ultraviolet CCD camera 5 or less.

Next a distance between adjacent peaks of two troughs is measured. The distance between peaks of two troughs corresponds a line width of the resist pattern 102. An obtained distance between peaks of two troughs (i.e., an observation value of a line width of the resist pattern 102) is different from an actual value (absolute value) of the line width of the resist pattern 102. However, since a substantially linear relationship exists between these values, the absolute value can be obtained by correcting an observation value of a line width of the resist pattern 102 if the ratio of an observation value to an absolute value of a line width of the resist pattern 102 is previously obtained with use of a scanning electron microscope (SEM) or the like.

As described above, a line width of the resist pattern 102 can be measured accurately in the order of nano-meter if a line width of the resist pattern 102 is obtained from an intensity profile prepared by the image processing computer 7. When the line width of the resist pattern 102 changes, the change of the line width can be detected with excellent accuracy.

In addition, in case where a pattern of a semiconductor integrated circuit includes a layered structure, positional dislocations of layering of patterns including the layered structure can be detected accurately by specifying pattern edges of a resist pattern corresponding to a lower pattern and pattern edges of a resist pattern corresponding to an upper pattern respectively, and by inspecting variants of these pattern edges.

If the resist pattern 102 to be inspected is a linear pattern, the line width can be measured more accurately by averaging inspection results of a plurality of lines. That is, there is a limit to reduction of shot noise caused by the ultraviolet CCD camera 5, and the shot noise therefore causes variants of the measurement accuracy between lines, in some cases. However, if inspection results of a plurality of lines are averaged and the average value is set as the line width of the resist pattern 102, the variants of the measurement accuracy between the lines can be averaged, so that the line width of the resist pattern 102 can be obtained more accurately.

Meanwhile, since this inspection apparatus 1 uses ultraviolet light as illumination light, it is difficult to make focus adjustment such that the distance between the ultraviolet objective lens 11 and the resist pattern 102 as an inspection target accurately corresponds to the focal length of the ultraviolet objective lens 11. Also, in this inspection apparatus 1, there is a case that the resist pattern 102 is inspected much more accurately if the resist pattern 102 is observed in an off-focus state slightly shifted from an on-focus state, depending on the size of the resist pattern 102 to be inspected.

Hence, in the inspection apparatus 1, coarse locus adjustment is carried out by the focus adjustment mechanism 16 described above. Thereafter, while the Z-stage of the movable stage 2 is moved finely to change slightly the position of the resist pattern 102 to be inspected, in the vertical direction or while the position of the ultraviolet objective lens 11 is slightly changed by the focus adjustment mechanism 16, an image of the resist pattern 102 is picked up at each position. An optimal image is selected from a plurality of picked-up images, and inspection of the resist pattern 102 is carried out based on this optimal image. In this manner, it is possible to carry out proper inspection by using effectively ultraviolet light having a short wavelength as illumination light.

As described above, in the inspection apparatus 1 to which the present invention is applied, the imaging magnification of the imaging optical system 6 is set such that the image resolution depending on the ultraviolet CCD camera 5 falls within a range from 10 nm to 30 nm on the resist pattern 102 to be inspected, i.e., the area of 10 to 30 nm on the resist pattern 102 corresponds to one pixel of the ultraviolet CCD camera 5. In addition, every time when the ultraviolet CCD camera 5 picks up an image, a deep ultraviolet laser beam having a short wavelength is irradiated on the resist pattern 102 to be inspected, at an irradiation light amount within a range from 0.5 mJ/cm² to an irradiation threshold value at which the resist pattern 102 as an inspection target is not caused to contract or at an irradiation threshold value at which the anti-reflection film 101 is not caused to change its absorption rate. Therefore, it is possible to inspect a very micro resist pattern 102 having a line width of, for example, about 150 nm with very high accuracy without causing contraction of the resist pattern 102 or deterioration of the anti-reflection film 101.

The above explanation has been made of the inspection apparatus 1 as an example in which a deep ultraviolet laser beam emitted from the ultraviolet solid laser device 3 as a light source is modulated by the acoustic optical modulator 4 thereby to control the irradiation light amount of the illumination light irradiated on the resist pattern 102 as an inspection target. However, the present invention is not limited to this example but a mechanical shutter means may be provided as a modulation means for modulating the illumination light, in place of the acoustic optical modulator 4. In this case, the irradiation light amount of the illumination light to be irradiated on the resist pattern 102 as an inspection target can be controlled to a proper value if open/close of the shutter means is controlled by the control computer 8 so as to adjust the amount of the illumination light which is transmitted through the shutter means. Also, the irradiation light amount of the illumination light can be controlled by switching on/off the ultraviolet solid laser device 3 as a light source through the control computer 8.

Although the example described above uses the ultraviolet solid laser 3 which emits a deep ultraviolet laser beam having a wavelength of about 266 nm as a light source, another light source may be used. However, in order to inspect a micro resist pattern 102 with excellent accuracy, illumination light having a shorter wavelength is more advantageous, and therefore, the present invention uses light having a wavelength of 355 nm or less within an ultraviolet range, as illumination light. Note that the ultraviolet laser beam having a wavelength of 355 nm is obtained as a triple wave of a YAG laser.

Also, in the example described above, inspection is made on a resist pattern for forming a pattern of a semiconductor integrated circuit. However, the present invention is not limited to the above example but may be applied effectively to inspection of all kinds of resist patterns that have a micro structure.

What is claimed is:

1. An inspection apparatus comprising:
   illumination means for irradiating a resist pattern as an inspection target with illumination light having a wavelength of 355 nm or less within an ultraviolet range;
   image pickup means for picking up an image of the resist pattern illuminated by the illumination means;
   an imaging optical system for forming an image of the resist pattern illuminated by the illumination means; and
   image processing means for processing the image of the resist pattern picked up by the image pickup means, wherein
   every time when the image pickup means picks up an image, the illumination means irradiates the resist pattern with the illumination light at an irradiation light amount within a range from 0.5 mJ/cm² to an irradiation threshold value at which the resist pattern is not caused to contract or an irradiation threshold value at which an absorption rate of an anti-reflection film provided near the resist pattern is not caused to change.

2. The inspection apparatus according to claim 1, wherein the illumination means comprises a light source for emitting the illumination light, and modulation means for modulating the illumination light emitted from the light source, so that every time when the image pickup means picks up an image, the illumination means irradiates the resist pattern with the illumination light at the irradiation light amount within the range from 0.5 mJ/cm² to the irradiation threshold value at which the resist pattern is not caused to contract or the irradiation threshold value at which the absorption rate of the anti-reflection film provided near the resist pattern is not caused to change.

3. The inspection apparatus according to claim 2, wherein the illumination means comprises, as the light source, an ultraviolet solid laser device for emitting illumination light having a wavelength of 266 nm.

4. The inspection apparatus according to claim 2, wherein the illumination means comprises an acoustic optical element as the modulation means.

5. The inspection apparatus according to claim 1, further comprising a cooled image pickup element as the image pickup means.

6. An inspection method in which illumination light is irradiated on a resist pattern as an inspection target with illumination light, an image of the resist pattern thus illuminated is picked up by image pickup means, and the image of the resist pattern picked up by the image pickup means is processed and analyzed, thereby to inspect a state of the resist pattern, wherein every time when the image pickup means picks up an image, the resist pattern is irradiated with illumination light having a wavelength of 355 nm or less within an ultraviolet range at an irradiation light amount within a range from 0.5 mJ/cm$^2$ to an irradiation threshold value at which the resist pattern is not caused to contract or an irradiation threshold value at which an absorption rate of an anti-reflection film provided near the resist pattern is not caused to change, and the image of the resist pattern illuminated with the illumination light is formed on the image pickup means with use of an image optical system in which an imaging magnification is set such that an image resolution of the image pickup means falls within a range from 10 nm to 30 nm.

7. The inspection method according to claim 6, wherein with use of a light source which emits the illumination light and modulation means which modulates the illumination light emitted from the light source, so that every time when the image pickup means picks up an image, the illumination means irradiates the resist pattern with the illumination light at the irradiation light amount within the range from 0.5 mJ/cm$^2$ to the irradiation threshold value at which the resist pattern is not caused to contract or the irradiation threshold value at which the absorption rate of the anti-reflection film provided near the resist pattern is not caused to change.

8. The inspection method according to claim 7, wherein an ultraviolet solid laser device which emits illumination light having a wavelength of 266 nm is used as the light source.

9. The inspection apparatus according to claim 7, wherein an acoustic optical element is used as the modulation means.

10. The inspection apparatus according to claim 6, wherein a cooled image pickup element is used as the image pickup means.

11. The inspection method according to claim 6, wherein the image of the resist pattern picked up by the image pickup means is processed and analyzed thereby to specify positions of edges of the resist pattern.

12. The inspection method according to claim 11, wherein a distance between positions of adjacent edges of the resist pattern is measured thereby to inspect a pattern width of the resist pattern.

13. The inspection method according to claim 11, wherein edge positions of a plurality of resist patterns corresponding to layers of a pattern having a layered structure are specified thereby to inspect a positional dislocation in layering of the pattern having the layered structure.

* * * * *